(12) United States Patent
Kyung-Hee Song et al.

(10) Patent No.: US 8,343,768 B2
(45) Date of Patent: Jan. 1, 2013

(54) INTEGRATOR SYSTEM AND METHOD FOR RAPIDLY DETERMINING EFFECTIVENESS OF A GERMICIDAL TREATMENT

(75) Inventors: Kevin Kyung-Hee Song, Tustin, CA (US); Benjamin Fryer, Lake Forest, CA (US); Peter Zhu, Cupertino, CA (US)

(73) Assignee: Ethicon, Inc., Somerville, NJ (US)

( * ) Notice: Subject to any disclaimer, the term of this patent is extended or adjusted under 35 U.S.C. 154(b) by 1603 days.

(21) Appl. No.: 11/527,273

(22) Filed: Sep. 26, 2006

(65) Prior Publication Data

US 2007/0092969 A1    Apr. 26, 2007

Related U.S. Application Data

(63) Continuation-in-part of application No. 11/093,529, filed on Mar. 30, 2005, now abandoned.

(51) Int. Cl.
*G01N 33/00* (2006.01)
(52) U.S. Cl. ............... 436/2; 436/56; 436/164; 422/28; 422/82.05; 702/22
(58) Field of Classification Search ............... 436/2, 56, 436/154; 422/28, 82.05; 702/22, 30
See application file for complete search history.

(56) References Cited

U.S. PATENT DOCUMENTS

| | | | |
|---|---|---|---|
| 4,328,182 A | 5/1982 | Blake | |
| 4,471,055 A | 9/1984 | Opp | |
| 4,521,376 A | 6/1985 | Witonsky et al. | |
| 5,486,459 A | 1/1996 | Burnham et al. | |
| 5,552,320 A | 9/1996 | Smith | |
| 5,942,438 A | 8/1999 | Antonoplos et al. | |
| 5,990,199 A | 11/1999 | Bealing et al. | |
| 6,355,448 B1 | 3/2002 | Foltz et al. | |
| 6,436,659 B1 | 8/2002 | Hui et al. | |
| 6,528,277 B1 | 3/2003 | Hendricks et al. | |
| 7,129,080 B2 | 10/2006 | Antloga et al. | |
| 2006/0228801 A1 | 10/2006 | Fryer et al. | |

FOREIGN PATENT DOCUMENTS

| | | |
|---|---|---|
| EP | 1256799 A2 | 11/2002 |
| JP | 7055796 A | 3/1995 |
| WO | WO 01/86289 A1 | 11/2001 |

OTHER PUBLICATIONS

European Search Report, Application No. 06251723.0, dated Oct. 24, 2007 (7 pages).

*Primary Examiner* — Lyle Alexander

(57) ABSTRACT

The effectiveness of an oxidative sterilization process is determined by exposing a known amount of a primary amine or aldehyde indicator chemical to an oxidative germicide. The oxidative germicide reacts with the indicator chemical. The amount of indicator chemical remaining after exposure to the germicide is determined by reacting the indicator chemical with a dye precursor chemical to form a colored product. The amount of indicator chemical remaining is determined from the intensity of the color of the colored product. The amount of indicator chemical remaining on the substrate is a measure of the effectiveness of the germicidal treatment. The dye precursor is an aldehyde when the indicator chemical is a primary amine and a primary amine when the indicator chemical is an aldehyde. An integrator for determining the effectiveness of the germicidal process includes an indicator chemical, where the indicator chemical is a primary amine or an aldehyde.

24 Claims, 6 Drawing Sheets

Colorimetric Kinetics of Glycine Tablet in Various [OPA]
@ 5 second; 2.5 mg/L of 59% H2O2

Colorimetric Kinetics of Glycine Tablet in 0.25% OPA
(@ 180 sec vs. 300 sec 2.5 mg/L of 59% H2O2)

INTEGRATOR SYSTEM AND METHOD FOR RAPIDLY DETERMINING EFFECTIVENESS OF A GERMICIDAL TREATMENT

This application is a continuation-in-part of U.S. application Ser. No. 11/093,529 filed Mar. 30, 2005 now abandoned, the entire contents of which are incorporated herein by reference.

BACKGROUND OF THE INVENTION

1. Field of the Invention

This invention relates to an integrator system and a method for rapidly determining the effectiveness of a germicidal process for medical equipment.

2. Background

Medical devices are sterilized before use in hospitals, physicians' offices, and other medical facilities. Steam, heat, ethylene oxide, and hydrogen peroxide are commonly used as sterilizing agents.

It is standard practice to include a sterility indicator in a load of articles to be sterilized in a sterilizer. The sterility indicator provides a measure of whether the sterilization process was effective in sterilizing the articles in a particular load. If the sterilization process was not effective, as indicated by the sterility indicator, the load of equipment is rejected for use.

Biological indicators are generally recognized as reliable sterility indicators. The biological indicator includes a carrier that has been inoculated with spores or other microorganisms. Spores are generally utilized in biological indicators, because spores are more resistant to sterilization than other microorganisms.

The biological indicator is placed into the sterilizer with the equipment to be sterilized. At the end of the sterilization process, the biological indicator is removed from the sterilizer, and the carrier is immersed in a sterile culture medium. The culture medium and carrier are incubated for a predetermined time at an appropriate temperature. At the end of the incubation period, it is determined whether any microorganisms have grown in the growth medium. If there is no growth of microorganisms in the growth medium, it is assumed that the equipment in the sterilizer has been properly sterilized. If microorganism growth is observed, the sterilization process was not effective, and the articles in the sterilizer are rejected for use. The growth of microorganisms is determined through a signal such as the generation of turbidity or a color change in a pH indicator due to a pH change from byproducts of cell growth in the medium. Biological indicators are described, for example, in U.S. Pat. Nos. 5,552,320 and 6,436,659, both of which are incorporated herein by reference in their entirety.

Although biological indicators are accurate indicators for the effectiveness of the sterilization cycle, at least 24-48 hours are required to obtain results from the biological indicators. The equipment that was exposed to the sterilization procedure is normally kept in quarantine until the results from the biological indicator are available. Medical equipment is expensive, and storage space in medical facilities is limited. Some hospitals therefore use the equipment before the results are available. Storing quarantined medical equipment is not an efficient use of resources. There is a need for a rapid test for determining the effectiveness of the sterilization process.

Foltz et al. (U.S. Pat. No. 6,355,448) describe a method of determining the effectiveness of a sterilization process by using the activity of enzymes rather than spores. It is stated that the enzyme test procedure requires only a few minutes rather than the several days that are required to obtain the results from biological indicators.

The use of a plurality of enzymes rather than a single enzyme was disclosed in U.S. Pat. Nos. 5,486,459 and 6,528,277. Using a plurality of enzymes was believed to better mimic the response of a microorganism than a single enzyme.

There is a need for sterilization indicators that provide sterilization results rapidly.

SUMMARY OF THE INVENTION

One aspect of the invention involves a method for rapidly determining the effectiveness of an oxidative germicidal process. The method includes providing a known amount of a first chemical, where the first chemical is selected from the group consisting of a primary amine, mixtures of primary amines, an aldehyde, and mixtures of aldehydes. The first chemical has a first color. The method also includes exposing the substrate and the first chemical to an oxidative germicide, thereby decreasing the known amount of the first chemical to a final amount. The final amount of the first chemical having the first color is contacted with a second chemical having a second color, thereby generating a third chemical having a third color. The intensity of the third color is related to the final amount of the first chemical on the substrate. The second chemical is a chemical selected from the group consisting of a primary amine and mixtures of primary amines when the first chemical is a chemical selected from the group consisting of an aldehyde and a mixture of aldehydes. The second chemical is a chemical selected from the group consisting of an aldehyde and a mixture of aldehydes when the first chemical is a chemical selected from the group consisting of a primary amine and a mixture of primary amines. The method also includes determining the intensity of the third color and determining the effectiveness of the germicidal process from the intensity of the third color.

Advantageously, the effectiveness of the germicidal process is determined by correlating the intensity of the third color with results from biological indicators. In an embodiment, the oxidative germicide is a sterilant. In an alternative embodiment, the oxidative germicide is a disinfectant.

In an embodiment, the oxidative germicide is a liquid, a vapor, or a gas. Advantageously, the intensity of the third color is determined visually. Preferably, the intensity of said third color is determined spectrophotometrically in the visible or ultraviolet region.

In an embodiment, at least one of the first chemical or the second chemical is colorless. Advantageously, the oxidative germicide is selected from the group consisting of hydrogen peroxide, peracetic acid, ethylene oxide, ozone, and chlorine dioxide. Preferably, the method also includes exposing the substrate and the oxidative germicide to plasma. In an embodiment, the percent completeness of the germicidal process is determined by comparing the intensity of the third color with the intensity of the color of a standard. Preferably, the primary amine is glycine or histidine, and the aldehyde is ortho-phthalaldehyde or glutaldehyde.

Another aspect of the invention involves an integrator for determining the effectiveness of a germicidal process with an oxidative germicide. The integrator includes a known amount of a first chemical, where the first chemical is selected from the group consisting of a primary amine, mixtures of primary amines, an aldehyde, and mixtures of aldehydes. The first chemical is in an enclosure. The first chemical is capable of reacting with the oxidative germicide when exposed to the oxidative germicide. The integrator also includes a reservoir of a second chemical, where the second chemical is a chemical selected from the group consisting of a primary amine and mixtures of primary amines when the first chemical is a chemical selected from the group consisting of an aldehyde and a mixture of aldehydes, and the second chemical is a chemical selected from the group consisting of an aldehyde and a mixture of aldehydes when the first chemical is a chemical selected from the group consisting of a primary amine and a mixture of primary amines. The second chemical is capable of reacting with the first chemical to form a third chemical having a color. The reservoir has a breakable barrier that isolates the second chemical from the first chemical and from the oxidative germicide during the contacting of the first chemical with the oxidative germicide. Breaking the breakable barrier in the reservoir contacts the second chemical with the first chemical, thereby forming the third chemical having the color. The reservoir is in the enclosure.

In an embodiment, the breakable barrier in the reservoir includes a frangible ampoule in the enclosure. Advantageously, the integrator also includes a second barrier, where the second barrier is inside the enclosure between the frangible ampoule and the first chemical. The second barrier in the enclosure is permeable to the second chemical. The second barrier prevents fragments from the frangible ampoule from contacting the first chemical.

In an embodiment, the integrator also includes a window in the enclosure, where the window is permeable to the oxidative germicide. The window allows the oxidative germicide to enter the enclosure. Advantageously, the primary amine is selected from the group consisting of glycine and histidine, and the aldehyde is selected from the group consisting of ortho-phthalaldehyde and glutaldehyde.

Preferably, the enclosure on the integrator also includes a transparent window, where the color change on the substrate can be observed through the transparent window visually or with a spectrophotometer.

DETAILED DESCRIPTION OF THE INVENTION

Figure 1:
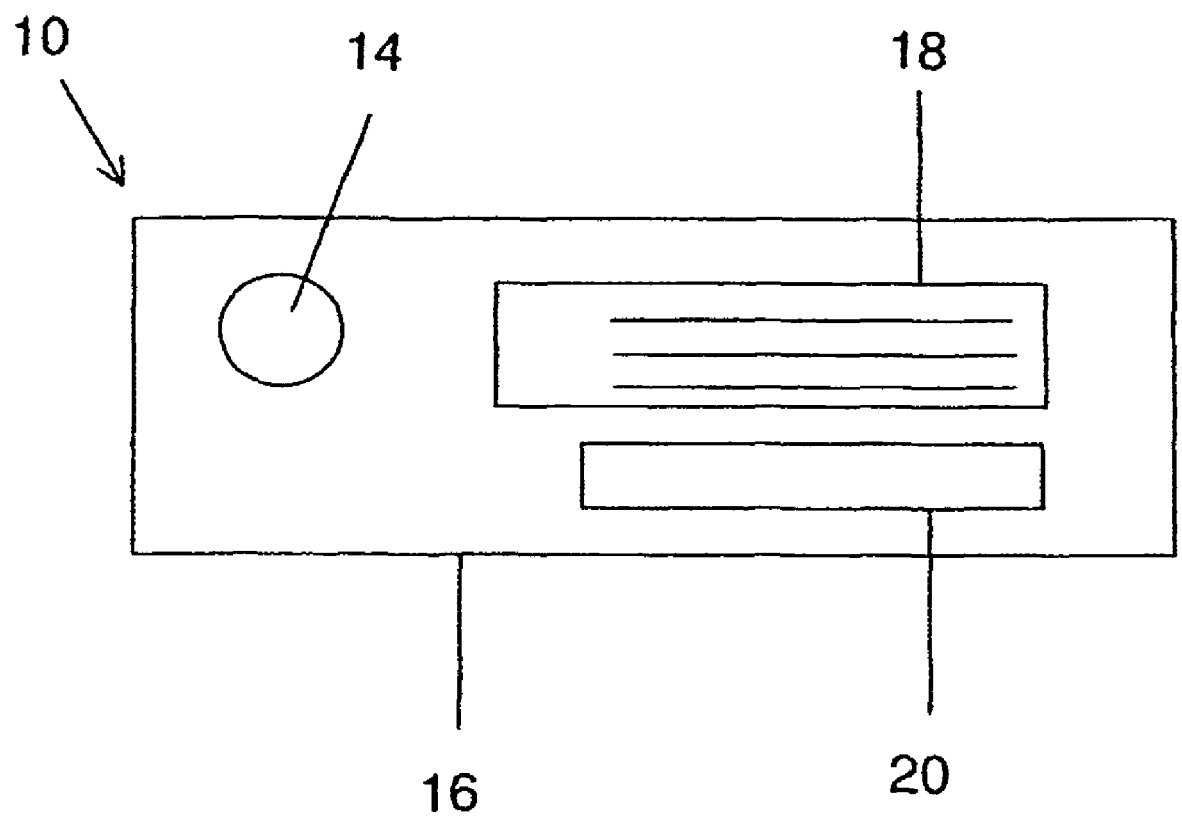
FIG. 1 is a schematic diagram of an integrator according to an embodiment of the present invention.

The term germicide as used herein is meant to include both sterilants and disinfectants. The term germicidal process as used herein includes both sterilization processes and disinfection processes. Sterilization indicators that utilize chemicals to mimic the resistance of a biological indicator (BI) have been termed as integrators. Integrators utilize an indicator chemical that responds to the germicide that is used in the germicidal process. The chemical reacts with the germicide in a repeatable manner and responds to the factors that are important to sterilization or disinfection in the germicidal process. The reaction of the indicator chemical with the germicide is integrated over time, and the amount of indicator chemical remaining on the integrator is correlated with the BI response.

Integrators integrate the reaction of the chemical over time in response to the critical parameters over a specified range of sterilization cycles.

The integrators and the method according to embodiments of the present invention provide results quickly, reproducibly, and accurately. The chemicals that are used in the integrators are inexpensive and stable. The results that are obtained from the integrators and the method according to embodiments of the present invention correlate well with the results from biological indicator tests.

The integrator according to embodiments of the present invention is meant to mimic the resistance of a biological indicator (BI) without using spores. The integrator according to an embodiment of the present invention includes an indicator chemical that reacts with an oxidative germicide. The integrator is suitable for oxidative germicides including hydrogen peroxide, peracetic acid, ethylene oxide, ozone, and chlorine dioxide. The oxidative germicides may be in the form of a liquid, a vapor, or a gas.

In an embodiment, plasma may be utilized in combination with the oxidative germicides to enhance the reaction of the oxidative germicides with the microorganisms in the chamber and the indicator chemical on the integrator and/or to break down the oxidative germicide after use. The use of plasma is optional.

The results from the integrator according to embodiments of the present invention are available quickly, approximately 30 seconds to approximately 5-6 minutes, depending on the chemicals selected for the integrators, compared to the 24-48 hours that are normally required to obtain results from a biological indicator.

Although described in the context of sterilization with a combination of hydrogen peroxide and plasma with the STERRAD® process, commercially available from Advanced Sterilization Products of Irvine, Calif., the integrator according to embodiments of the present invention may be used with a variety of germicidal processes. The description of germicidal processes such as sterilization or disinfection with hydrogen peroxide and plasma through the STERRAD® process is illustrative only and is not meant to be limiting.

The integrator according to embodiments of the present invention contains an indicator chemical. The indicator chemical reacts with the germicide and responds to the factors that are important for sterilization. The amount of indicator chemical that remains on the integrator after exposure to the germicide can be correlated with the response of BI's that are placed into the sterilization chamber together with the integrator. The response of a BI is a generally accepted measure of the effectiveness of a germicidal process. The response of a BI in the sterilization chamber can be correlated with response of the integrators to "calibrate" the response of the integrators with the response of a biological indicator.

In an embodiment, primary amines or aldehydes are used as indicator chemicals in integrators according to embodiments of the present invention. Oxidative germicides react with both primary amines and aldehydes. Both primary amines and aldehydes are suitable indicator chemicals for integrators according to embodiments of the present invention.

The amount of the primary amine indicator chemical or the aldehyde indicator chemical that remains on the integrator after the germicide process can be used to determine the effectiveness of the sterilization or disinfection process for the load that is treated in the sterilizer.

The amount of primary amine indicator chemical or aldehyde indicator chemical that remains on the integrator can be measured in a variety of ways such as instrumental methods, chemical analysis, etc. Any suitable method of measuring the concentration of the primary amine indicator chemical or the aldehyde indicator chemical is suitable.

In an embodiment, the completeness of the germicidal process may be conveniently determined by observing a change in color in the integrator.

Many primary amines react with aldehydes to form colored products. The amount of primary amine indicator chemical or the amount of aldehyde indicator chemical remaining on the integrator after exposure to the oxidative germicide can be determined from the intensity of the color of the product of the reaction of an aldehyde with a primary amine.

As used herein, an aldehyde that is contacted with a primary amine indicator chemical or a primary amine that is contacted with an aldehyde indicator chemical is termed a "dye precursor", because the product of the reaction of a primary amine with an aldehyde is colored, a "dye", even if neither the primary amine nor the aldehyde has a color.

The primary amine and the aldehyde can change roles, depending on which chemical is utilized as the indicator chemical in the integrator. In an embodiment in which a primary amine is the indicator chemical, the dye precursor is an aldehyde. In an embodiment in which an aldehyde is the indicator chemical, the dye precursor is a primary amine.

The intensity of the color of the colored product resulting from the reaction of the primary amine with the aldehyde can be used to determine the effectiveness of the treatment of the load with the oxidative germicide.

In an embodiment, an integrator according to an embodiment of the present invention contains a first chemical having a first color, where the first chemical is an indicator chemical. The indicator chemical is selected from the group consisting of a primary amine, a mixture of primary amines, an aldehyde, and a mixture of aldehydes.

The integrator containing the indicator chemical is placed into a sterilizer with a load of equipment that is to be treated. The load and integrator are contacted with an oxidative germicide in a sterilizer. The oxidative germicide reacts with the indicator chemical, decreasing the amount of indicator chemical remaining on the integrator. The amount of indicator chemical remaining on the integrator after the contacting with the oxidative germicide is a measure of the effectiveness of the germicidal treatment with the oxidative germicide.

At a point when the effectiveness of the treatment with the oxidative germicide is to be determined, the integrator containing the first chemical having the first color is contacted with a second chemical having a second color. The first chemical having the first color is the indicator chemical. The second chemical having the second color is the dye precursor. The dye precursor is a chemical selected from the group consisting of a primary amine, a mixture of primary amines, an aldehyde, and a mixture of aldehydes. Primary amines may not be mixed with aldehydes to form the dye precursor. In an embodiment where the first chemical, the indicator chemical, is a primary amine or a mixture of primary amines, the second chemical, the dye precursor, is an aldehyde or a mixture of aldehydes. In an embodiment where the first chemical, the indicator chemical, is an aldehyde or a mixture of aldehydes, the second chemical, the dye precursor, is a primary amine or a mixture of primary amines.

The product from the reaction of the first chemical, the indicator chemical, with the second chemical, the dye precursor, is a third chemical having a third color. The intensity of the third color of the third chemical resulting from the reaction of the first chemical with the second chemical can be used to determine how much of the first chemical, the indicator chemical, remains on the integrator. The amount of the first chemical indicator chemical that remains on the integrator is a measure of how effective the treatment with the oxidative germicide was. If only a small amount of the first chemical indicator chemical remains on the integrator, the intensity of the third color due to the third chemical is low. A low intensity of the third color is an indication that the treatment with the oxidative germicide was effective.

In an embodiment, the degree of completeness of the treatment with the oxidative germicide can be determined from the intensity of the third color due to the third chemical, the product of the reaction of the first chemical indicator compound with the second chemical dye precursor. The indicator compound on the integrator, the first compound, reacts with the oxidative germicide in parallel with the germicidal treatment of the load in the sterilization chamber. The intensity of the third color due to the third chemical resulting from the reaction of the first chemical indicator chemical with the second chemical dye precursor decreases as the amount of the indicator chemical decreases due to the reaction with the oxidative germicide.

The intensity of the third color can be correlated with results from biological indicators that are placed into the sterilization chamber together with the indicators. The intensity of the third color can be correlated with the percent sterilization or percent disinfection, as determined from biological indicators. The percent sterilization or disinfection can therefore be determined from the intensity of the third color due to the third compound.

In an embodiment, the first chemical, the indicator chemical, is placed on a substrate for ease of handling. The substrate can be a variety of materials. The substrate can be an absorbing substrate or a nonabsorbing substrate. Absorbing substrates absorb the germicide. Nonabsorbing substrates absorb little or none of the germicide.

Filter paper is an absorbing substrate, because filter paper absorbs the germicide. A glass filter disk is a nonabsorbing substrate, because the glass filter disk does not absorb significant quantities of the germicide and is thus preferred.

The indicator chemical can be packaged in a water-soluble binder such as an acrylic polymer or carboxymethylcellulose. The indicator chemical and water-soluble binder can be applied to the surface of the integrator or sterility indicator by, for example, ink jet printing a solution of the indicator chemical and the water-soluble binder onto the surface of an inert backing material.

Absorbing substrates absorb germicide during the germicidal process. When the second chemical dye precursor is contacted with the absorbing substrate, the absorbed germicide on the absorbing substrate can react with the dye precursor. Oxidative germicides generally react with primary amines and aldehydes, the two forms of dye precursor. It is therefore generally advantageous to use excess second chemical primary amine or aldehyde dye precursor when the substrate is an absorbing substrate, because the absorbed germicide reacts with the dye precursor when the dye precursor is contacted with the absorbing substrate.

In an embodiment, the integrator containing the indicator chemical is placed in the sterilizer with the equipment to be sterilized and is exposed to the germicide. The indicator chemical reacts with the germicide, reducing the initial concentration of the indicator chemical from an initial value to a final value.

After the germicidal process is complete, the integrator containing the first chemical indicator chemical is exposed to the second chemical dye precursor. If any indicator chemical is still present, contacting the indicator chemical with the dye precursor forms the third compound having the third color. If significant color develops on the integrator, the germicidal cycle is judged to have not been effective.

It is generally preferred that the second chemical dye precursor be contacted with the integrator after the conclusion of the cycle, because the dye precursor reacts with the germicide. If the dye precursor is contacted with the integrator before the conclusion of the cycle, the germicide will react with the second chemical dye precursor, and it may be necessary to add dye precursor to provide sufficient dye precursor to cause a color change from the reaction of the second chemical dye precursor with the first chemical indicator chemical, forming the third chemical having the third color. The second chemical dye precursor is therefore generally contacted with the integrator at the end of the cycle. In an embodiment, the cycle may be a canceled cycle.

In an embodiment, the second chemical is isolated from the germicide until the conclusion of the cycle. Isolating the second chemical dye precursor from the germicide protects the second chemical from reacting with the germicide and being destroyed.

The color change from the reaction of the first chemical indicator chemical with the second chemical dye precursor to form the third chemical having the third color can be determined visually. Because a visual change is somewhat subjective, the color change is generally determined with an optical detector. The optical detector for the color change resulting from the reaction of the first chemical indicator chemical with the second chemical dye precursor can operate at visible or ultraviolet wavelengths.

The primary amine may be any suitable primary amine. In an embodiment, the primary amine is an amino acid. In an embodiment, the primary amine is selected from the group consisting of arginine, histidine, and combinations thereof. Other suitable primary amines include the following amino acids: alanine, proline, amino-caproic acid, phenylalanine, tryptophan, methionine, glycine, serine, cysteine, tyrosine, glutamine, aspartic acid, glutamic acid, lysine, arginine, and histidine. Peptides or polypeptides formed from any number or type or amino acids are also suitable primary amines.

Arginine is an exemplary primary amine indicator chemical. Arginine gives a strong, rapid color change when exposed to aldehydes. Arginine also reacts rapidly with germicides. Arginine is a water-soluble solid that is conveniently weighed, dissolved in a solvent, and applied to the substrate or other support. Other primary amines can be used in other embodiments, as will become clear in the description and the Examples below.

Arginine has structure I, below.

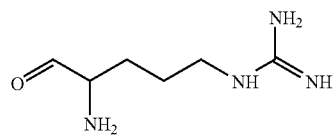

I

The NH$_2$ groups are primary amine groups. The NH groups are secondary amine groups. Aldehydes often do not react with secondary amine groups.

The aldehyde may be any aldehyde that reacts with primary amines but not secondary or tertiary amines to produce a color. Aldehydes such as OPA (ortho-phthalaldehyde), glutaldehyde, and aromatic aldehydes are suitable. Other aldehydes are also suitable.

FIG. 1 shows a diagram of an integrator system 10 according to an embodiment of the present invention. The integrator system 10 of FIG. 1 includes integrator chemistry 14 located on integrator strip 16, where the integrator strip 16 is an inert material for supporting the integrator chemistry 14. The integrator strip 16 is generally made of a material that does not react with or adsorb the germicide. The integrator chemistry 14 includes a first chemical, the indicator chemical. The integrator strip 16 is a substrate for the integrator chemistry 14.

Peel off label 18 is optionally located on the integrator strip 16. Information on the sterilization cycle can be written on the peel off label 18, and the peel off label 18 with the information on the sterilization cycle can be placed into a sterilization logbook. Chemical indicator strip 20 contains a chemical that undergoes a color change when exposed to the germicide. A color change in chemical indicator strip 20 simply shows that the chemical indicator strip 20 has been exposed to the germicide. The chemical indicator strip 20 is not an indicator of the effectiveness of sterilization but is simply an indicator as to whether the chemical indicator strip 20 has been exposed to germicide.

The color change on the chemical indicator strip 20 shows the operator that the integrator system 10 should not be used again. Bordeaux Red changes color when exposed to hydrogen peroxide. Other dyes can be used on the chemical indicator strip 20 to indicate exposure to other germicides. Suitable dyes are described, for example, in U.S. Pat. No. 5,942,438, which is incorporated herein by reference in its entirety.

After the cycle, the integrator chemistry 14 portion of the integrator strip 16 is exposed to the second chemical, the dye precursor. The second chemical dye precursor reacts with the first chemical indicator chemical on the integrator chemistry 14 to form the third chemical having the third color. The presence of a significant amount of color on the integrator chemistry 14 on integrator strip 16 after exposure of the integrator chemistry 14 to the second chemical dye precursor indicates that the cycle was not effective.

Figure 2:
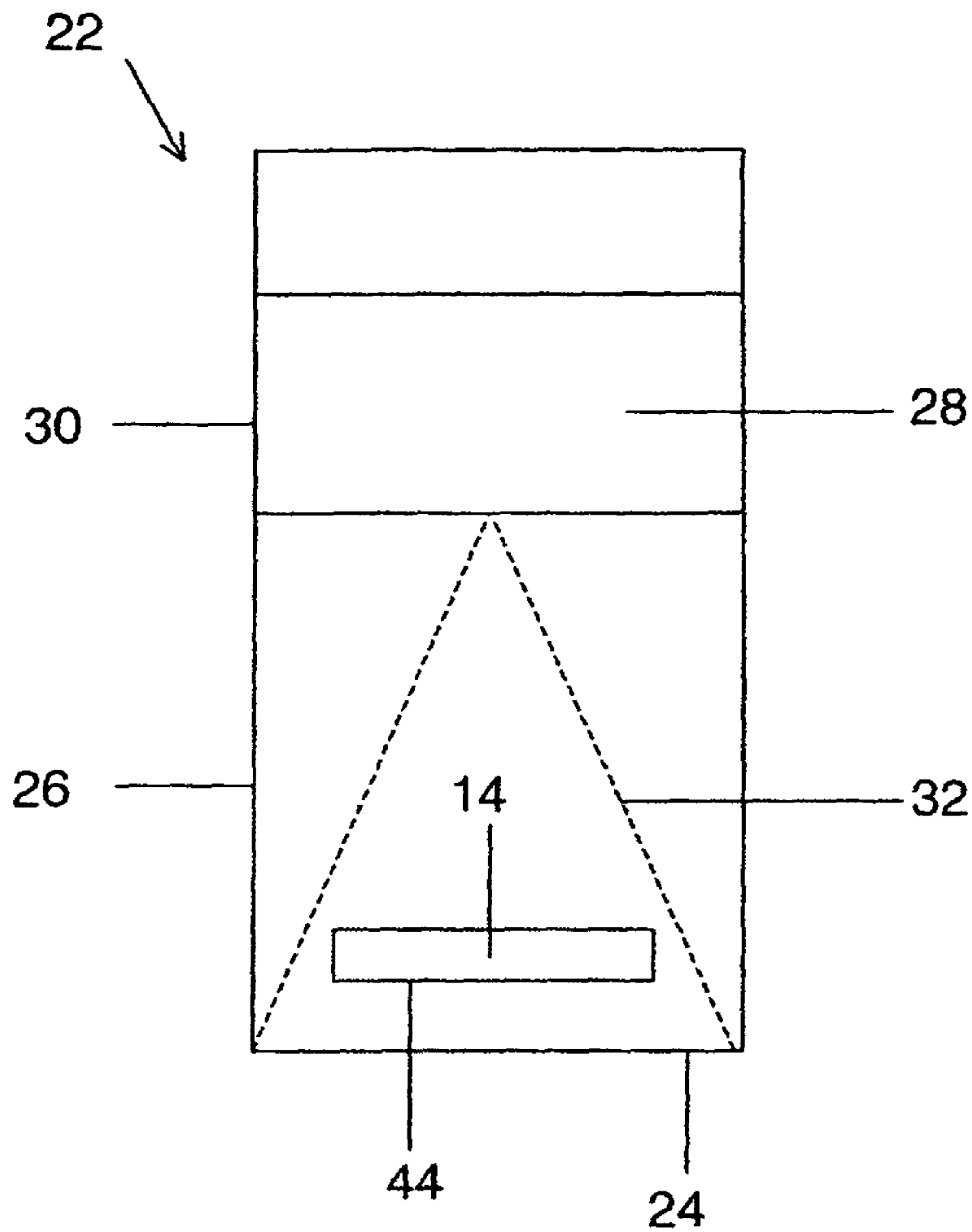
FIG. 2 is a schematic diagram of a compressible integrator system containing an integrator according to an embodiment of the present invention.

FIG. 2 shows a compressible integrator system 22. Compressible integrator system 22 of FIG. 2 includes integrator chemistry 14 on substrate 44 located in container 26. Gas permeable surface 24 allows the germicide to enter container 26 and contact the integrator chemistry 14.

The dye precursor 28 is contained in reservoir 30. Supports 32 are located adjacent to reservoir 30. Reservoir 30 protects the dye precursor from being destroyed by reacting with the oxidative germicide during the germicidal cycle.

After the cycle, compressible integrator system 22 is crushed or squeezed. Supports 32 pierce the reservoir 30, and the second chemical dye precursor 28 that was contained in the reservoir 30 contacts the integrator chemistry 14. The second chemical dye precursor reacts with any first chemical indicator chemical that remains after the cycle. If any first chemical indicator chemical remains on the substrate 44, the first chemical indicator chemical in the integrator chemistry 14 reacts with the second chemical dye precursor to form the third chemical having the third color on the substrate 44, indicating that the germicidal process was incomplete. A lack of color on the integrator chemistry 14 indicates that the germicidal treatment was successful.

Figure 3:
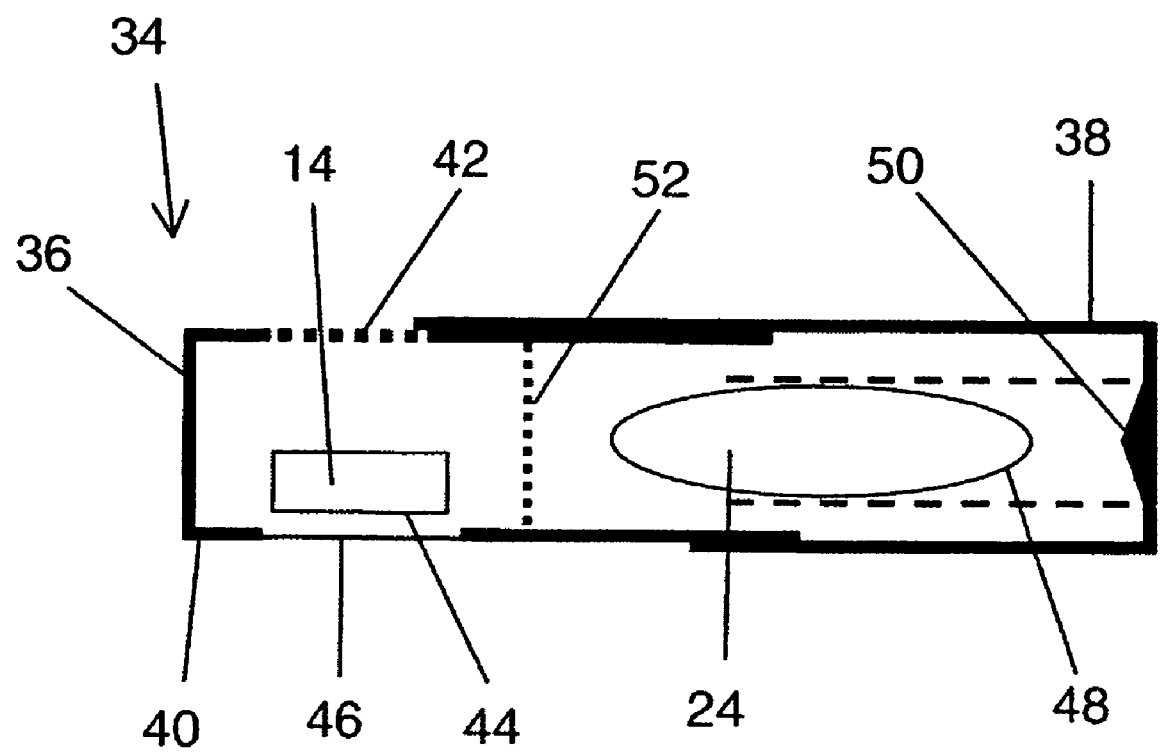
FIG. 3 is a schematic diagram of a slidable integrator system containing an integrator according to an embodiment of the present invention.

FIG. 3 shows a schematic diagram of a slidable integrator system 34. Slidable integrator system 34 includes closable sliding container 36. The closable sliding container 36 is formed of outer shell 38 and inner shell 40. Outer shell 38 slides over inner shell 40. Sliding outer shell 38 over inner shell 40 opens window 42 in closable sliding container 36. Window 42 allows germicide to enter the interior of closable sliding container 36. The germicide may be a liquid, a vapor, or a gas.

The closable sliding container 36 contains substrate 44 supporting integrator chemistry 14. The integrator chemistry 14 includes the first chemical, the indicator chemical. Substrate 44 is located adjacent transparent window 46 on inner shell 40. Any color change in the substrate 44 can be observed through transparent window 46. Substrate 44 is the substrate for the indicator chemistry 14. The indicator chemistry 14 includes the first chemical, the indicator chemical. In an embodiment, substrate 44 is a glass filter, a nonabsorbing substrate.

The second chemical, the dye precursor 24, is contained in crushable ampoule 48 inside closable sliding container 36. Crushable ampoule 48 is made of a frangible material such as glass. Crushable ampoule 48 protects the second chemical, the dye precursor 24, from being destroyed by the germicide during the germicidal process.

Wedge 50 is attached to an inside of outer shell 38 of the closable sliding container 36. Wedge 50 is a projection on the inside of the outer shell 38. In an embodiment wedge 50 has a sharp edge to aid in penetrating the crushable ampoule 48. Barrier 52 is located inside closable sliding container 34 between crushable ampoule 48 and substrate 44. Barrier 52 prevents fragments of crushable ampoule 48 from interfering with the reading of substrate 44. Barrier 52 is permeable to the second chemical, the dye precursor 24. When crushable ampoule 48 is crushed, the second chemical, the dye precursor, is released and can flow through barrier 52 to contact the first chemical indicator chemical on substrate 44. In an embodiment, barrier 52 is a wire screen.

Figure 4:
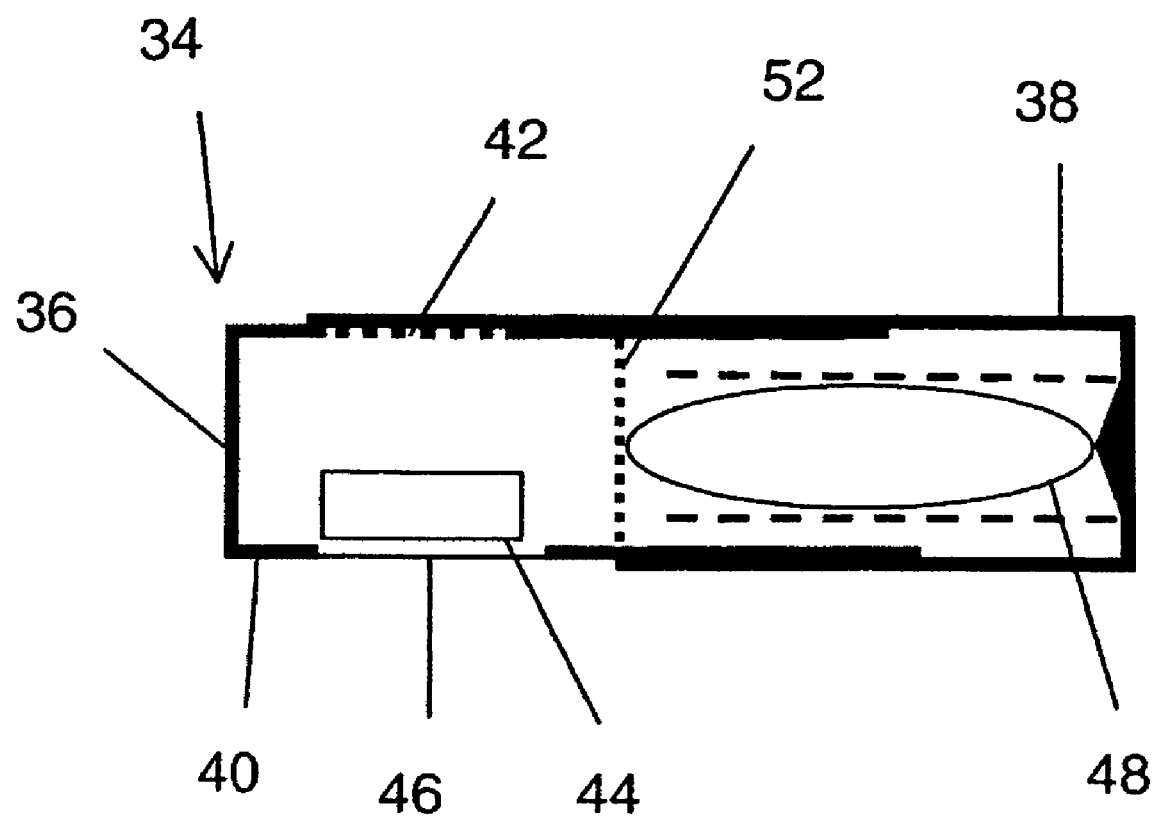
FIG. 4 is a schematic diagram of the slidable integrator system of FIG. 3 after an outer shell has been moved over an inner shell of a closable sliding container on the slidable integrator system.

FIG. 4 shows a schematic diagram of the slidable integrator system 34 and closable sliding container 36 of FIG. 3 after the conclusion of the cycle. The outer shell 38 of the closable sliding container 36 in FIG. 4 has been moved toward the left of FIG. 4 by sliding outer shell 38 over inner shell 40.

Sliding outer shell 38 over inner shell 40 has several effects, as shown in FIG. 4. First, sliding outer shell 38 over inner shell 40 closes window 42. Closing window 42 isolates closable sliding container 36, retaining the second chemical dye precursor inside the closable sliding container 36. The second chemical dye precursor can stain the hands of the operator. Second, sliding the outer shell 38 over inner shell 40 forces wedge 50 into contact with crushable ampoule 48, pushing the crushable ampoule 48 into contact with barrier 52, crushing the crushable ampoule 48. Crushing the crushable ampoule 48 releases the second chemical, the dye precursor 24. The second chemical dye precursor 24 that is released flows though barrier 52 and contacts the substrate 44.

If any first chemical indicator chemical remains on the substrate 44 when the second chemical dye precursor 24 contacts the substrate 44, the second chemical dye precursor 24 reacts with the first chemical indicator chemical in the integrator chemistry 14 to form the third chemical having a third color. The third color is distinctive and readily distinguished from the first color of the first chemical and the second color of the second chemical. Barrier 52 prevents fragments of the crushable ampoule 48 from contacting the substrate 44 and interfering with the determination. The color change on the substrate 44 can be observed through transparent window 46.

Rather than employ the substrate 44, an integrator system can employ a tablet of the first chemical, thereby eliminating the need for a separate substrate. Such a tablet can be substituted for the substrate bearing the first chemical in any of the preceding examples. The tablet can be pelletized with or without various binder materials, lubricants or other ingredients such as cellulosics, fiber, starch, agar, serum, alcohols, sugars, bicarbonates, acids, polymers and the like which are known or may be known in the art to enhance and control its physical integrity, porosity, density, solubility, wet-ability, thermostability, and reaction rater.

Figure 5:
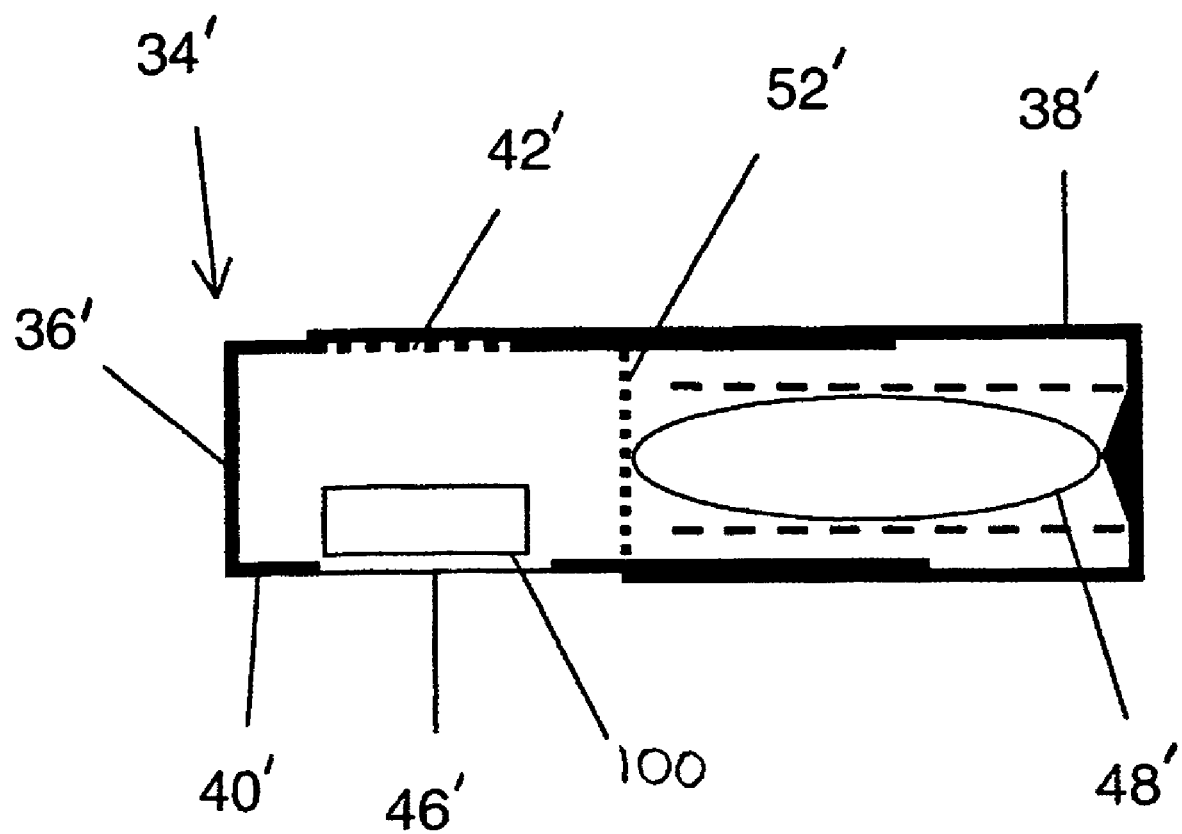
FIG. 5 is a schematic diagram of the integrator system of FIG. 4 employing a tablet.

FIG. 5 shows an integrator system 34' which is the same as that of FIG. 4 with the exception that the substrate 44 has been replaced by a tablet 100. All part numbers shown with a prime symbol refer to the like part in FIG. 4.

Method of Using the Integrator

The integrator according to an embodiment of the present invention is placed into the sterilization chamber with the load that is to be sterilized, and the germicidal cycle is run. After the completion of the sterilization cycle, the second chemical dye precursor is contacted with the integrator. The second chemical, the dye precursor, reacts with any first chemical indicator chemical remaining on the integrator to produce the third chemical having the third color. The color that is produced depends on the structure of the first chemical indicator chemical and the second chemical dye precursor. The intensity of the color depends on the amount of first chemical indicator chemical that remains on the integrator and on the concentration of the second chemical dye precursor.

If color develops on the integrator within a predetermined time period, such as approximately 5-6 minutes after the second chemical dye precursor is added to the integrator, the sterilization cycle is judged to have been ineffective.

The intensity of the color on the integrator may be judged visually by comparing to a color standard, or the intensity of the color may be measured spectrophotometrically in the visible or ultraviolet region. Judging the color intensity visually is more subjective than measuring the color intensity with an instrument.

The second chemical dye precursor may be contacted with the integrator in various manners. In an embodiment, the second chemical dye precursor is contacted with the integrator manually using a pipette, an eyedropper, or other suitable device.

Manual addition of the second chemical dye precursor is appropriate with an integrator such as the integrator shown in FIG. 1, where there is no method of protecting the second chemical dye precursor from being exposed to and being destroyed by the germicide during the sterilization cycle.

FIGS. 2 and 3 show embodiments of integrators where the second chemical dye precursor is present in the integrator during the sterilization cycle but is protected from exposure to the germicide by being enclosed in a reservoir or a crushable ampoule. Other means of protecting the second chemical dye precursor from being exposed to the germicide may be used in other embodiments.

The following examples are meant to be illustrative only and are not meant to be limiting on the scope.

EXAMPLES

Example 1

Results of Tests with an Integrator Containing Arginine as the Indicator Chemical With Varying Injection Volumes of Hydrogen Peroxide A series of integrators was prepared by contacting paper disks with an aqueous solution of arginine. The integrators were placed in a STERRAD® 50 sterilizer with a load of equipment to be sterilized and several biological indicators. The paper disks are absorbing substrates.

The sterilizer was evacuated to 0.8 torr. Plasma was produced in the chamber for 15 minutes to condition the load. The sterilizer was evacuated further to 0.4 torr, and hydrogen peroxide was injected and contacted with the load, integrators, and biological indicators for 6 minutes.

The sterilizer was vented with air for 2 minutes. The sterilizer was evacuated again to 0.5 torr, and plasma was produced for an additional 2 minutes. The plasma power was 400 watts for both plasma exposures.

The paper integrator disks were contacted with 100 μL of a 5% solution of ortho-phthalaldehyde (OPA) dye precursor after the germicide cycle, and the response of the integrators was measured visually after the integrators had been contacted with the OPA. The results are shown in Table 1 below.

TABLE 1

Integrator and Biological Indicator Test Results

| Hydrogen Peroxide Injection Volume μL | Biological Indicator Results | Integrator Color Intensity |
|---|---|---|
| 100 | 100% positive | Dark orange color in 3 minutes |
| 250 | 40% positive | Orange color after 5-6 minutes, a few are colorless |
| 400 | 0% positive | 10-15% show faint color after 5-6 minutes |
| 500 | 0% positive | No color |

The cycles with 100 and 250 μL of hydrogen peroxide were ineffective, as shown by the positive biological indicator results. The integrator results were consistent with the biological indicator results, because the integrators for the cycles with 100 and 250 μL of hydrogen peroxide had significant color within 3-6 minutes after being contacted with the OPA. The color is the result of a reaction between unreacted arginine, the primary amine indicator compound, and OPA, the aldehyde dye precursor.

In the sterilization cycle with 400 μL of hydrogen peroxide, 10-15% of the integrators developed a faint color after 5-6 minutes. None of the biological indicators in this run were positive. The faint color that developed on the integrators after 5-6 minutes is a showing that the integrators provide a more stringent measure of the degree of sterilization than the biological indicators.

None of the biological indicators in the run with 500 μL of hydrogen peroxide were positive. None of the integrators had any color. Both the biological indicator results and the integrator results are consistent in showing that the sterilization cycle with 500 μL of hydrogen peroxide was effective.

The data from the integrators according to an embodiment of the present invention were consistent with the data from the biological indicators. However, the results from the integrators were available in 5-6 minutes, compared to 24-48 hours for the biological indicator results.

Example 2

Integrator Response Measured With a Spectrometer

Non adsorbent glass fiber disks were impregnated with an aqueous solution of arginine. The glass fiber disks are non-absorbing substrates. The disks were placed in a STERRAD® 50 sterilizer and processed under the same conditions as in Example 1 with varying injection volumes of hydrogen peroxide. The quantities of hydrogen peroxide are shown in Table 2 below.

The glass fiber disks were contacted with 50 μL of a 5% aqueous solution of OPA dye precursor after the cycle was complete. The intensity of light absorption of the disks was determined with a TAOS TCS230EVM evaluation module color sensor (Parallax, Rocklin, Calif.) at approximately 470 nm, approximately 550 nm, and approximately 610 nm (red, green, and blue wavelengths).

Hydrogen peroxide injection volumes of 50, 300, and 1000 μL were used. All of the BI's would be negative with a hydrogen peroxide injection of 300 μL in the STERRAD® 50 sterilizer. Table 2 summarizes the color intensities at the 610 nm (blue) wavelength. The integrator responses shown in Table 2 are the differences between the initial reading and the final reading at 30 seconds after addition of OPA. Large numbers for the integrator response indicate more color and less effective sterilization.

TABLE 2

| Hydrogen Peroxide Injection Volume (μL) | Integrator Response (Range) for Samples |
|---|---|
| 1000 | 5-17 |
| 300 | 28-47 |
| 50 | 58-85 |

Small numbers in the integrator response indicate effective sterilization. The range of 5-17 in the integrator response for the samples that were exposed to 1000 μL of hydrogen peroxide is consistent with effective sterilization. The integrator response range of 28-47 for the samples that were exposed to 300 μL of hydrogen peroxide is consistent with effective sterilization.

The integrator response range of 58-85 for the samples that were exposed to 50 μL of hydrogen peroxide indicates significant color, showing ineffective sterilization.

The results of Example 2 demonstrate that the results from the integrators according to embodiments of the present invention can be measured effectively with a spectrophotometer rather than visually, as in Example 1.

Example 3

Integrator Tests With Histidine as the Indicator Chemical and OPA as the Dye Precursor Histidine rather than arginine was used as the primary amine indicator chemical to form a series of integrators in Example 3. An aqueous solution of histidine was placed on a series of glass fiber disks to form integrators according to an alternative embodiment of the present invention.

The integrators were placed into a standard STERRAD® 50 validation load, and cycles were run as described in Examples 1 and 2.

Cycles were run with 0 μL of hydrogen peroxide and 300 μL of hydrogen peroxide. The integrators were contacted with 50 μL of a 5 volume % solution of OPA at the end of the sterilization process. The intensity of the third color of the third compound on the integrators was measured with the TAOS color sensor described in Example 2.

A combination of red, green, and blue (RGB) wavelengths (470, 550, and 610 nm) were used to measure the response, because the color of the product of histidine and OPA is different than the color of the product of arginine and OPA. A root mean square (RMS) of the absorption was calculated for all three wavelengths measured by the sensor.

The light absorption results were consistent with the treatment with 0 μL of hydrogen peroxide being ineffective at sterilization and the treatment with 300 μL of hydrogen peroxide being effective at sterilization. The example demonstrates that histidine can be used as a primary amine indicator compound in place of arginine. A wide variety of primary amines can be used as primary amine indicator compounds.

Example 4

Integrator Tests with Histidine and Glutaraldehyde

A series of integrators was prepared with histidine as the indicator chemical on glass fiber disks as the substrate. The integrators were processed in a STERRAD® 50 sterilizer under the same conditions as in Example 3. Glutaraldehyde rather than OPA was contacted with the processed integrators as the aldehyde dye precursor. The results are shown in Table 4 below.

TABLE 4

Results From Integrator Tests With Histidine and Glutaraldehyde

| Volume of Hydrogen Peroxide (μL) | Range in the Change in Red Wavelength Reading (Change = Initial Color Reading − Color Reading at 30 Seconds) |
|---|---|
| 0 | 11-29 |
| 300 | 0-7 |

The small change in light absorption from the start time to the finish time for the integrators that were exposed to 300 μL of hydrogen peroxide demonstrates that the sterilization with 300 μL of hydrogen peroxide was effective.

The large change in light absorption from the start time to the reading at 30 seconds for the integrators that were exposed to a volume of 0 μL of hydrogen peroxide is a showing that the sterilization was not effective.

The results of Example 4 are a demonstration that glutaraldehyde can be used as an aldehyde dye precursor in place of OPA Example 5

Integrators with OPA as the Indicator Chemical

A series of integrators are prepared with OPA as the indicator chemical. The indicators are placed into a sterilizer with a load to be sterilized and a series of biological indicators. The load, biological indicators, and integrators are contacted with 100-500 μL of hydrogen peroxide under the conditions described in Example 1.

The integrators with OPA as the indicator chemical are contacted with an aqueous solution of arginine as the dye precursor. The results from the integrators with OPA as an aldehyde indicator chemical and arginine as a primary amine dye precursor correlate well with the results from the biological indicators.

The results from Example 5 demonstrate that aldehydes such as OPA can be used as the indicator chemical with primary amines such as arginine as the dye precursor.

Example 6

Integrators with Amino Acid Tablet

Rather than employ the amino acid onto a substrate, a tablet was formed by pelletizing with a tablet press Glycine into pellets 4 mm in diameter and 0.85 mm in thickness and containing approximately 15.6 mg of Glycine powder. The tablets were placed into glass vials with a semi-permeable barrier and processed in a hydrogen peroxide gas sterilization cycle at 5.0 mg/L concentration of 59% $H_2O_2$ with an exposure of 300 seconds and at a pressure of approximately 7 Torr. After the cycle, 200 μl of a 0.5% OPA solution was added into the sample vial and color changes were observed. A positive control was also prepared using 200 μl of a 0.5% OPA solution to an unprocessed sample tablet. The positive control visibly changed color (clear to yellow to green) within 10 seconds of the addition of the OPA and continued to turn to dark green/black. All processed samples did not change color and remained clear after Glycine tablet dissolved.

Example 7

Integrators with Amino Acid Tablet—OPA Concentration Varied

Figure 6:
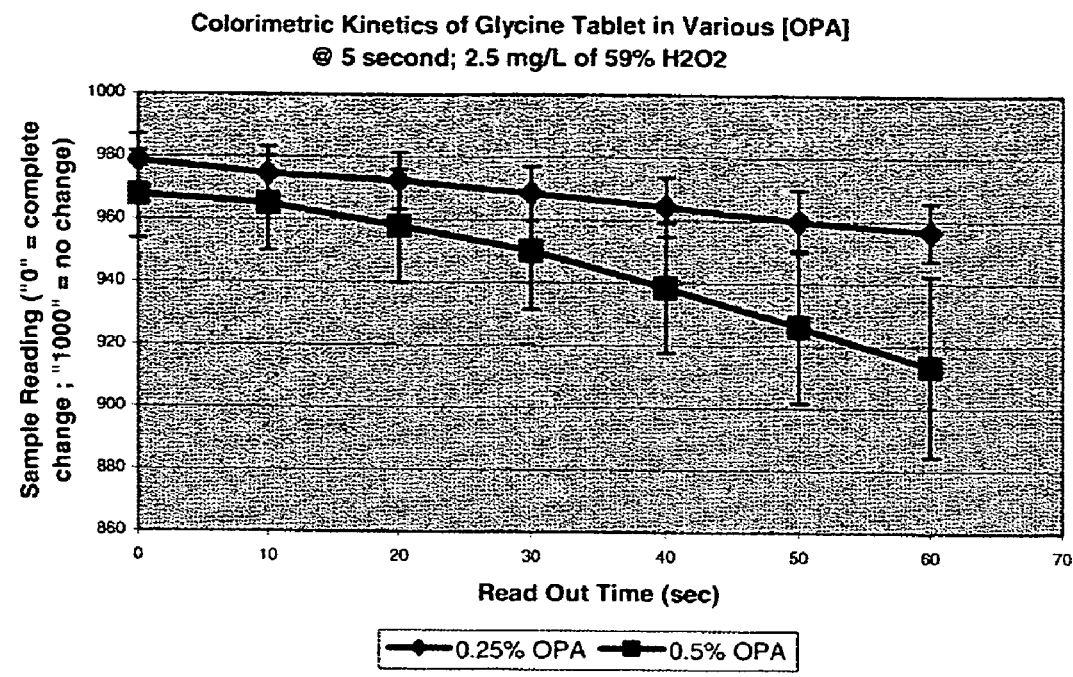
FIG. 6 is a graph of the results of Example 7.

Glycine tablets prepared according to Example 6 were subjected to various concentration of OPA solution (0.25%, & 0.5%) after being exposed to 2.5 mg/L of 59% $H_2O_2$ vapor for 5 second (5 second exposure is not sufficient to destroy the reactivity of Glycine tablet). Their colorimetric responses were measured with RBG digital fiberoptic sensor (colorimeter) in 10-second intervals and plotted in the graph of FIG. 6. The results show that the reaction rate is OPA concentration dependant.

Example 8

Integrators with Amino Acid Tablet—OPA Concentration Varied

Figure 7:
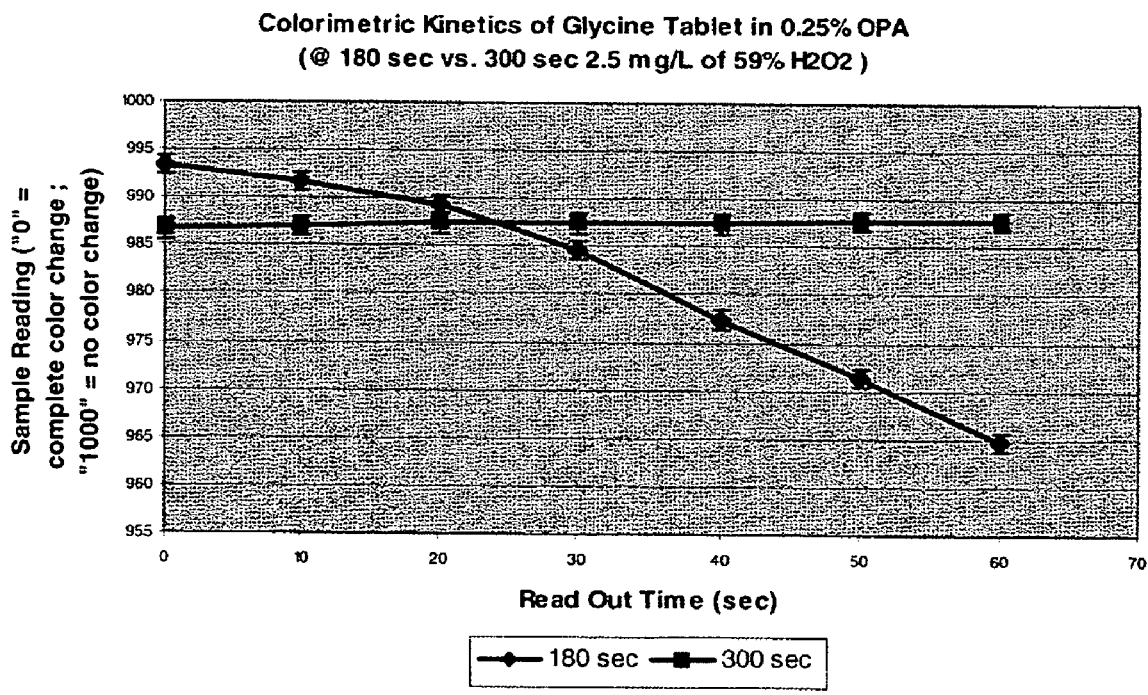
FIG. 7 is a graph of the results of Example 8.

Glycine tablets prepared according to Example 6 were exposed to various levels of hydrogen peroxide exposure and their colorimetric responses were observed. Glycine tablets were exposed to 2.5 mg/L of 59% hydrogen peroxide vapor for 180 seconds and 300 seconds. Then, 0.25% OPA solution was added to observe the color change. Kinetics of color development was measured with RBG digital fiberoptic sensor (colorimeter) in 10-second interval. These measurements from 180 second and 300 second exposures were compared and analyzed, with the results being plotted on the graph of FIG. 7. These results show that Glycine tablets can be inactivated and no longer reactive to OPA solution after being exposed to adequate amount of hydrogen peroxide vapor sterilization. The reactivity and absence of reactivity can be measured and differentiated, thus forming the basis of an integrator system according to the present invention.

The integrator according to embodiments of the present invention allows the effectiveness of the sterilization process to be determined rapidly.

Various modifications and alterations of this invention will be apparent to those skilled in the art without departing from the scope and spirit of this invention. It is to be understood that the invention is not limited to the embodiments disclosed therein, and that the claims should be interpreted as broadly as the prior art allows.

What is claimed is:

1. A method for determining the effectiveness of an oxidative germicidal process, the method comprising:
testing the oxidative germicidal process by treating a known amount of a first chemical with an oxidative germicide selected from the group consisting of hydrogen peroxide, peracetic acid, ethylene oxide, ozone, and chlorine dioxide, the oxidative germicide thereby decreasing the known amount of the first chemical to a final amount of the first chemical; wherein the first chemical has a first color and is selected from a first group consisting of at least one primary amine or a second group consisting of at least one aldehyde that reacts with the at least one primary amine;
contacting the final amount of the first chemical having the first color with a second chemical having a second color, wherein the second chemical is a chemical selected from the first group when the first chemical is a chemical selected from the second group or wherein the second chemical is a chemical selected from the second group when the first chemical is a chemical selected from the first group;
producing a third chemical compound having a third color, the third color having an intensity, wherein the intensity of the third color is related to the final amount of the first chemical;
determining the intensity of the third color; and
determining the effectiveness of the oxidative germicidal process from the intensity of the third color.

2. The method of claim 1, wherein the step of determining the effectiveness of the oxidative germicidal process comprises correlating the intensity of the third color with results from biological indicators.

3. The method of claim 1, wherein the oxidative germicide is a sterilant.

4. The method of claim 1, wherein the oxidative germicide is a disinfectant.

5. The method of claim 1, wherein the first chemical is pelletized into a powdered tablet.

6. The method of claim 5, wherein the first chemical is glycine.

7. The method of claim 1, wherein the intensity of the third color is determined spectrophotometrically in the visible or ultraviolet region.

8. The method of claim 1, further comprising exposing the oxidative germicide to plasma.

9. The method of claim 1, wherein a percent completeness of the germicidal process is determined by comparing the intensity of the third color with an intensity of a color of a standard.

10. The method of claim 1, wherein the primary amine is selected from the group consisting of glycine and histidine and the aldehyde is selected from the group consisting of ortho-phtalaldehyde and glutaldehyde.

11. The method of claim 1, wherein the determining the intensity occurs in 6 minutes or less.

12. The method of claim 1, wherein the method is a quantitative method for determining the effectiveness of an oxidative germicidal process.

13. The method of claim 1, wherein the method occurs in a sterilization chamber.

14. The method of claim 1, wherein the first chemical is on a substrate.

15. The method of claim 14, wherein the substrate is a solid substrate.

16. A method for determining the effectiveness of an oxidative germicidal process, the method comprising:
treating a known amount of a first chemical with an oxidative germicide selected from the group consisting of hydrogen peroxide, peracetic acid, ethylene oxide, ozone, and chlorine dioxide, the oxidative germicide thereby decreasing the known amount of the first chemical to a final amount of the first chemical; wherein the first chemical has a first color and is selected from a first group consisting of at least one primary amine or a second group consisting of at least one aldehyde that reacts with the at least one primary amine;
contacting the final amount of the first chemical having the first color with a second chemical having a second color, wherein the second chemical is a chemical selected from the first group when the first chemical is a chemical selected from the second group or wherein the second chemical is a chemical selected from the second group when the first chemical is a chemical selected from the first group;
producing a third chemical compound having a third color, the third color having an intensity, wherein the intensity of the third color is related to the final amount of the first chemical;
determining the intensity of the third color; and
determining the effectiveness of the oxidative germicidal process from the intensity of the third color.

17. A method for determining the effectiveness of an oxidative germicidal process, the method comprising:
testing the oxidative germicidal process by treating a known amount of at least one primary amine with an oxidative germicide selected from the group consisting of hydrogen peroxide, peracetic acid, ethylene oxide, ozone, and chlorine dioxide thereby decreasing the known amount of the at least one primary amine to a final amount;
wherein the at least one primary amine has a first color;
contacting the final amount of the at least one primary amine having the first color with at least one aldehyde that reacts with the at least one primary amine having a second color to produce a chemical compound;
the chemical compound having a third color, the third color having an intensity, wherein the intensity of the third color is related to the final amount of the at least one primary amine;
determining the intensity of the third color; and
determining the effectiveness of the oxidative germicidal process from the intensity of the third color.

18. The method of claim 17, wherein the primary amine is selected from the group consisting of an amino acid, arginine, histidine, alanine, proline, amino-caproic acid, phenylalanine, tryptophan, methionine, glycine, serine, cysteine, tyrosine, glutamine, aspartic acid, glutamic acid, lysine, arginine, and histidine, peptides, polypeptides, and combinations thereof.

19. The method of claim 18, wherein the aldehyde does not react with secondary or tertiary amines.

20. The method of claim 18, wherein the aldehyde is selected from the group consisting of ortho-phthalaldehyde, glutaldehyde, and aromatic aldehydes.

21. A method for determining the effectiveness of an oxidative germicidal process, the method comprising:
testing the oxidative germicidal process by treating a known amount of at least one aldehyde with an oxidative germicide selected from the group consisting of hydrogen peroxide, peracetic acid, ethylene oxide, ozone, and chlorine dioxide thereby decreasing the known amount of the at least one aldehyde to a final amount; wherein the at least one aldehyde has a first color;

contacting the final amount of the at least one aldehyde having the first color with at least one primary amine that reacts with the at least one aldehyde having a second color to produce a chemical compound;

the chemical compound having a third color, the third color having an intensity, wherein the intensity of the third color is related to the final amount of the at least one aldehyde;

determining the intensity of the third color; and determining the effectiveness of the oxidative germicidal process from the intensity of the third color.

22. The method of claim 21, wherein the primary amine is selected from the group consisting of an amino acid, arginine, histidine, alanine, proline, amino-caproic acid, phenylalanine, tryptophan, methionine, glycine, serine, cysteine, tyrosine, glutamine, aspartic acid, glutamic acid, lysine, arginine, and histidine, peptides, polypeptides, and combinations thereof.

23. The method of claim 22, wherein the aldehyde does not react with secondary or tertiary amines.

24. The method of claim 22, wherein the aldehyde is selected from the group consisting of ortho-phthalaldehyde, glutaldehyde, and aromatic aldehydes.

* * * * *